United States Patent [19]

Takenaka et al.

[11] Patent Number: 4,476,335

[45] Date of Patent: Oct. 9, 1984

[54] PROCESS FOR PREPARING MONONITROCHLOROBENZENE

[75] Inventors: Shinji Takenaka; Takeshi Nishida; Joshiro Kanemoto, all of Fukuoka, Japan

[73] Assignee: Mitsui Toatsu Chemicals, Inc., Tokyo, Japan

[21] Appl. No.: 445,587

[22] Filed: Nov. 30, 1982

[30] Foreign Application Priority Data

Dec. 1, 1981 [JP] Japan ............................... 56-191772

[51] Int. Cl.³ ............................................. C07C 79/12
[52] U.S. Cl. .................................................. 568/937
[58] Field of Search ........................................ 568/937

[56] References Cited

U.S. PATENT DOCUMENTS 3,957,890  5/1976  Schumacher .................. 568/937
3,979,467  9/1976  Schumacher .................. 568/937

Primary Examiner—Leland A. Sebastian
Attorney, Agent, or Firm—Albert L. Jeffers; Douglas L. Miller

[57] ABSTRACT

In a process for the preparation of mononitrochlorobenzene by nitration of chlorobenzene using a mixed acid of nitric acid and phosphoric acid, the nitration reaction is carried out by using a molar ratio of nitric acid to chlorobenzene of not more than equimol in the presence of a concentrated phosphoric acid as the phosphoric acid component at temperatures of 50°–120° C. while maintaining the concentration of phosphoric acid to 72.4 weight % as $P_2O_5$ or more during the reaction.

5 Claims, 3 Drawing Figures

PROCESS FOR PREPARING MONONITROCHLOROBENZENE

BACKGROUND OF THE INVENTION

This invention relates to a process for the preparation of mononitrochlorobenzene by nitration of chlorobenzene using a mixed acid of nitric acid and a concentrated phosphoric acid as the nitrating agent.

Mononitrochlorobenzene having three types of isomers is used as intermediates for dyestuffs, agricultural chemicals and other industrial chemicals.

In conventional methods for the nitration of chlorobenzene, a mixed acid of nitric acid and sulfuric acid has been in general employed as the nitrating agent using the molar ratio of nitric acid to chlorobenzene of about equimol at elevated temperatures. A method using a mixed acid of nitric acid and phosphoric acid is also known.

In the method using the mixed acid of nitric acid and sulfuric acid, due to the dehydrating effect of sulfuric acid on water resulting from the nitration, mononitrochlorobenzene is effectively obtained, however there is a disadvantage that the side reaction to dinitration is promoted with an increase in yields. The formation of dinitrochlorobenzene lowers a purity of mononitrochlobenzene and also, is in danger of exploding during the reaction and subsequent refining steps. Therefore, this by-formation must be controlled to the utmost and the limit of tolerance is 1,000 ppm in general. Accordingly, in case of the nitric/sulfuric mixed acid method a yield relative to nitric acid is controlled to about 95% at most. Also, in this method the nitration reaction product includes a majority of ortho- and para-compounds and a meta-compound of less than 1% and the ratio of para-compound to ortho-compound is about 2.

In the industrial production of mononitrochlorobenzene, it is desirable to alter the isomer ratio in accordance with the demand. It is possible to obtain the para-/ortho ratio of less than 2 by selecting reaction conditions. For example, it is known that the para/ortho ratio is reduced with elevating of reaction temperature, however in the nitric/sulfuric mixed acid method the by-formation of dinitrochlorobenzene is still more increased at elevated temperatures and therefore, the nitration at elevated temperatures must be avoided. Thus, in case of the nitric/sulfuric mixed acid method there is a limit in altering the para/ortho ratio.

On the other hand, according to the method using a mixed acid of nitric acid and phosphoric acid as the nitrating agent, the para/ortho ratio is lowered as compared with the case of the nitric/sulfuric mixed acid, but the yield of end products is extremely reduced. If the reaction is carried out under an elevated temperature and pressure to increase the yield, the formation of dinitrochlorobenzene is increased though not so large as in the nitric/sulfuric mixed acid method.

Thus, in a commercial scale, the method using the nitric/sulfuric mixed acid is usually employed.

As to other methods for lowering the para/ortho ratio in the nitration reaction of chlorobenzene, there is provided a method of adding phosphoric acid to the nitrating agent (Japanese Patent Publication No. 52-42783). According to this method, the para/ortho ratio can be successively lowered by increasing the amount of phosphoric acid from 1.63 in case of non-addition to about 1.2. This patent specification discloses a method using a nitric/phosphoric mixed acid in which phosphoric acid is used in the range of 0.90-2.56 molar ratio relative to chlorobenzene and in which, for example, the nitration is carried out using 2 mols of phosphoric acid and 1 mol of nitric acid relative to 1 mol of chlorobenzene, however the yield is only about 80% even at the reaction temperature elevated to 100° C. The reason of this low yield is considered as being as follows:

In the above method orthophosphoric acid ($H_3PO_4$) is added in an amount sufficient for using for the mixed acid component as well as altering the para/ortho ratio and therefore, an aqueous phosphoric acid solution of low concentration is present in large quantities in the reaction system. Also, phosphoric acid used instead of sulfuric acid as the mixed acid component is inferior to sulfuric acid in the dehydrating effect on the resulting water increasing with the progress of reaction. Thus the nitration reaction velocity is lowered.

There is provided an improved method of adding such a polyvalent metal catalyst as molybdenum, manganese, vanadium and tungsten to the nitric/phosphoric mixed acid thereby increasing the yield (Japanese Patent Publication No. 52-46928). However, even this method is less than 95% in yield and further, there is an environmental pollution by the waste fluid due to use of the heavy metals.

Besides, there are provided a method using nitric acid and sulfonic acid (U.S. Pat. No. 3,077,502), a method using a solid catalyst having a sulfoxydifluoromethyl group (Japanese Patent Kokai No. 50-154212) and a method using a molecular sieve catalyst and nitrogen dioxide as the nitrating agent in vapour phase (Japanese Patent Kokai No. 54-95521). These methods are disadvantageous in commercial scale in view of costs, complicatedness or yield.

SUMMARY OF THE INVENTION

An object of this invention is to provide a process for the preparation of mononitrochlorobenzene by nitration of chlorobenzene using a nitric/phosphoric mixed acid thereby attaining a high yield of more than 95% and controlling by-formation of dinitrochlorobenzene.

In accordance with this invention there is provided a process for the preparation of mononitrochlorobenzene by nitration of chlorobenzene using a mixed acid of nitric acid and phosphoric acid as the nitrating agent, which comprises using a molar ratio of nitric acid to chlorobenzene of not more than equimol in the presence of a concentrated phosphoric acid as the phosphoric acid component and carrying out the nitration reaction at temperatures of 50°-120° C. while maintaining the concentration of phosphoric acid to 72.4% by weight as $P_2O_5$ or more during the reaction.

BRIEF EXPLANATION OF THE DRAWINGS

In FIGS. 1, 2 and 3 Curve A represents the process of this invention and Curve B a conventional method.

DETAILED DESCRIPTION OF THE INVENTION

According to the process of this invention, mononitrochlorobenzene is obtained with a high yield of more than 95%, preferably 98% while controlling the by-production of dinitrochlorobenzene to the grade of less than 500 ppm relative to mononitrochlorobenzene.

Figure 1:
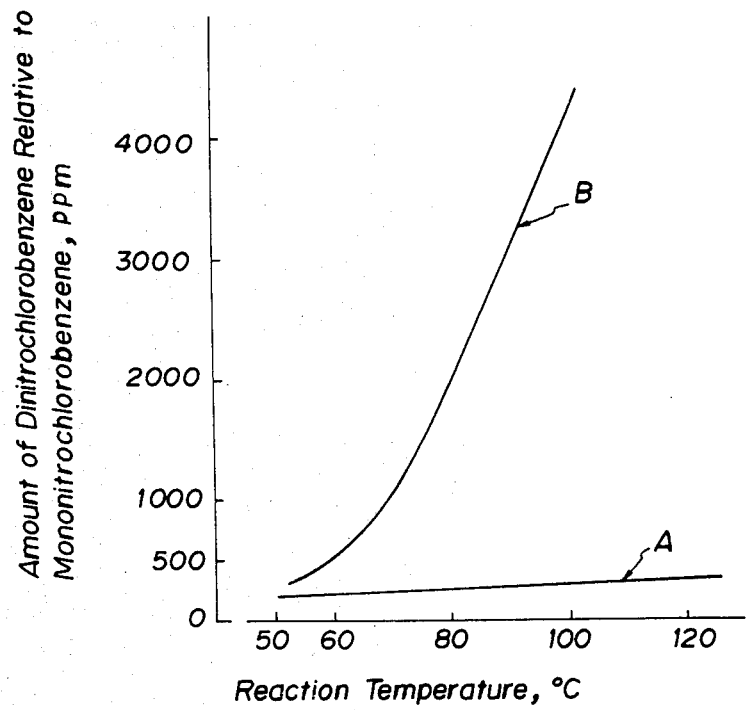
FIG. 1 is a graph representing a relationship between the nitration reaction temperature and the amount of dinitrochlorobenzene by-produced.

In FIG. 1 Curve B represents a conventional method using the nitric/sulfuric mixed acid as the nitrating agent, in which the nitration is carried out using 1 mol of nitric acid and 1.5 mols of sulfuric acid relative to 1 mol of chlorobenzene. Curve A represents the process of Example 1 using a concentrated phosphoric acid as the phosphoric acid component according to this invention, in which a concentrated phosphoric acid having 76.5% of $P_2O_5$ is used and 0.8 mols of nitric acid and 1.77 mols of phosphoric acid calculated as $P_2O_5$ are used relative to 1 mol of chlorobenzene.

Figure 2:
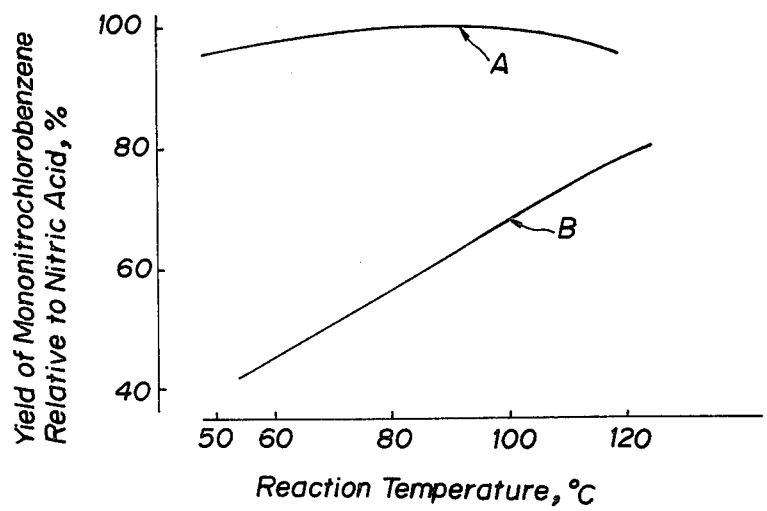
FIG. 2 is a graph representing a relationship between the reaction temperature and the yield of mononitrochlorobenzene relative to nitric acid.

In FIG. 2 Curve B represents a conventional method using 1 mol of a commercially available orthophosphoric acid ($H_3PO_4$) having 61.5% of $P_2O_5$ and 1 mol of nitric acid relative to 1 mol of chlorobenzene. Curve A represents the process of Example 1 according to this invention identical with Curve A in FIG. 1.

Figure 3:
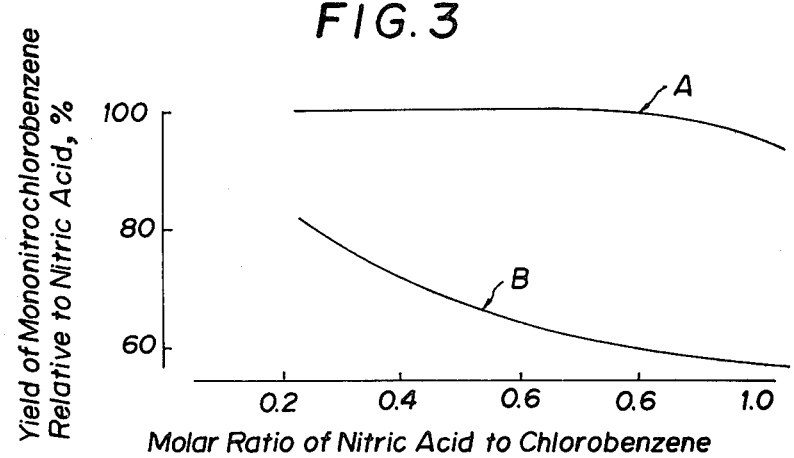
FIG. 3 is a graph representing a relationship between the molar ratio of nitric acid to chlorobenzene and the yield of mononitrochlorobenzene relative to nitric acid at the reaction temperature of 80° C.

In FIG. 3 Curve B represents an example using the commercially available orthophosphoric acid in the same amount and concentration as Curve B of FIG. 2 and Curve A represents an example using the concentrated phosphoric acid ($P_2O_5$ 76.5%) in the same amount as Curve A of FIG. 2.

The process of this invention has been found on the basis of the knowledges obtained from these drawings.

The modes of embodiment of this invention are as follows:

The concentrated phosphoric acid which may be used in this invention can be easily obtained by vapourizing and concentrating a normal orthophosphoric acid. A commercially available orthophosphoric acid has a phosphoric acid concentration of 85-89% (61.5-64.4% by weight as $P_2O_5$) at the utmost. The concentrated phosphoric acid used herein means one having a phosphoric acid concentration of more than 100%, i.e. 72.4% by weight as $P_2O_5$ or more, preferably 74-80% by weight as $P_2O_5$. The concentrated phosphoric acid thus obtained is a mixture containing various condensed phosphoric acids (e.g. pyrophosphoric acid, tripolyphosphoric acid and tetrapolyphosphoric acid) in addition to phosphoric acid. These compositions vary depending on impurities in phosphoric acid and the degree of concentration, though as far as the $P_2O_5$ content is 72.4% or more the desired effects of this invention can be attained. It is possible to attain the effects of this invention by using only one component of the above-mentioned condensed phosphoric acids as the concentrated phosphoric acid, however it is difficult to economically produce them in form of a single compound. It is preferred that the concentrated phosphoric acid after concentration is used in form of a mixture. The vapourization and concentration is effectively carried out by heating under reduced pressure and the desired concentration of $P_2O_5$ is approximately determined by the heating temperature. For example, a 74% $P_2O_5$ requires about 130° C. and a 80% $P_2O_5$ about 180° C.

The nitration according to this invention may be carried out by reacting chlorobenzene with nitric acid in the presence of the above-mentioned concentrated phosphoric acid. The concentration of phosphoric acid during the reaction should be maintained so that the phosphoric acid concentration in waste acids after completion of the reaction does not lower to the grade of less than 72.4% by weight whereby mononitrochlorobenzene can be obtained with a high yield. Therefore, the concentration and amount of the concentrated phosphoric acid to be added are preliminarily determined taking the amount of chlorobenzene and the amount of nitric acid into consideration. The concentration of the concentrated phosphoric acid is 72.4 wt.% or more as $P_2O_5$, preferably 74-80 wt.%. For example, in case of reacting 46 g (0.72 mols) of a 98% nitric acid with 100 g (0.9 mols) of chlorobenzene, a concentrated phosphoric acid having 75 wt.% of $P_2O_5$ is used in the amount of 356 g or more, and for a concentrated phosphoric acid having 80 wt.% of $P_2O_5$, 122 g or more is used.

The reaction temperature is between preferably 50° and 120° C., more preferably 60° and 100° C. The process of this invention may be carried out at temperatures over 120° C. thereby controlling the by-production of the dinitro compound, though about 120° C. is a limit for effecting a reaction under normal pressure. At elevated temperatures the yield relative to nitric acid is reduced and the formation of the dinitro compound is increased. On the other hand, with less than 50° C. the desired high yield can not be obtained.

Nitric acid used in the reaction has a concentration of preferably, 95% or more. The amount is equimol or less relative to chlorobenzene, preferably 0.2-0.8 mol ratio. With more than equimol the yield relative to nitric acid is reduced and the recovery step of nitric acid becomes expensive.

The reaction is carried out in the presence of the concentrated phosphoric acid having a specific concentration according to this invention whereby a high yield relative to nitric acid of more than 98%, about 100% can be obtained in a short time. After completion of the reaction chlorobenzene can be easily recovered by distillation, but the recovery of nitric acid is difficult. In the conventional methods, since the yield relative to nitric acid is 95% at most, complicated steps for dealing with unreacted nitric acid are required. According to this invention, however, since the yield relative to nitric acid is approximately 100%, such complicated steps are not required.

Further, as mentioned above, the by-production of the dinitro compound is controlled by addition of the concentrated phosphoric acid and accordingly, reaction temperatures which do not influence the yield can be set within a comparatively broad range so that the para-compound/ortho-compound ratio can be altered in accordance with the demand.

This invention will be illustrated by the following non-limitative Examples. Percentages in Examples are based on weight.

EXAMPLE 1

A concentrated phosphoric acid of 76.5% as $P_2O_5$ was obtained by concentrating a commercially available 85% orthophosphoric acid at 150° C. under 20 mmHg. Next, 100 g (0.9 mols) of chlorobenzene were vigorously stirred at 80° C. and a mixture of 46 g (0.72 mols) of a 98% nitric acid and 297 g of the above concentrated phosphoric acid was dropped over 10 minutes. Thereafter reaction was continued at 80° C. for an hour and a half. After completion of the reaction the stirring was stopped and the organic phase was separated from the waste acid phase.

| Yield of mononitrochlorobenzene relative to HNO$_3$: | 99.5 |
|---|---|
| Para/ortho ratio: | 1.3 |
| Dinitrochlorobenzene relative to mononitrochlorobenzene: | 200 ppm |
| P$_2$O$_5$ concentration in waste acids: | 73.3% |

EXAMPLE 2

100 g (0.9 mols) of chlorobenzene were vigorously stirred at 100° C. and a mixed acid consisting of 23 g (0.36 mols) of a 98% nitric acid and 290 g of the same concentrated phosphoric acid as in Example 1 was dropped over 10 minutes. Thereafter reaction was continued at 100° C. for an hour and a half.

| Yield: | 99.5% |
|---|---|
| Para/ortho ratio: | 1.0 |
| Dinitro compound: | 250 ppm |
| P$_2$O$_5$ conc. in waste acids: | 74.8% |

EXAMPLE 3

100 g (0.9 mols) of chlorobenzene were vigorously stirred at 60° C. and a mixed acid consisting of 57 g (0.9 mols) of a 98% nitric acid and 294 g of the same concentrated phosphoric acid as in Example 1 was dropped over 10 minutes. Thereafter reaction was continued at 60° C. for an hour and a half.

| Yield: | 98% |
|---|---|
| Para/ortho ratio: | 1.5 |
| Dinitro compound: | 200 ppm |
| P$_2$O$_5$ conc. in waste acids: | 72.5% |

EXAMPLE 4

A concentrated phosphoric acid of 80% as P$_2$O$_5$ was obtained by concentrating a commercially available 85% phosphoric acid under 180° C./20 mmHg. Next, 100 g (0.9 mols) of chlorobenzene were vigorously stirred at 120° C. and a mixed acid consisting of 23 g (0.36 mols) of a 98% nitric acid and 99 g of the above concentrated phosphoric acid was dropped over 10 minutes. Thereafter reaction was continued at 120° C. for an hour and a half.

| Yield: | 99.5% |
|---|---|
| Para/ortho ratio: | 0.9 |
| Dinitro compound: | 300 ppm |
| P$_2$O$_5$ conc. in waste acids: | 75% |

What is claimed is:

1. A process for the preparation of mononitrochlorobenzene by nitration of chlorobenzene using a mixed acid of nitric acid and phosphoric acid as the nitrating agent, which comprises using a molar ratio of nitric acid to chlorobenzene of not more than equimol in the presence of a concentrated phosphoric acid as the phosphoric acid component and carrying out the nitration reaction at temperatures of 50°–120° C. while maintaining the concentration of phosphoric acid to 72.4% by weight as P$_2$O$_5$ or more during the reaction, the concentrated phosphoric acid containing various condensed phosphoric acids obtained by vapourizing and concentrating a normal orthophosphoric acid.

2. The process of claim 1 wherein the concentrated phosphoric acid has a concentration of 74–80% by weight as P$_2$O$_5$.

3. The process of claim 1 wherein the reaction is carried out at temperatures of 60°–100° C.

4. The process of claim 1 wherein nitric acid is used in the amount of 0.2–0.8 molar ratio relative to chlorobenzene.

5. The process of claim 1 wherein the reaction is carried out so that the yield of mononitrochlorobenzene relative to nitric acid amounts to 98% or more.

* * * * *